United States Patent
Thibaut et al.

(10) Patent No.: US 10,478,390 B2
(45) Date of Patent: Nov. 19, 2019

(54) USE OF GLYCOSIDES TO INCREASE HAIR MASS

(71) Applicant: L'OREAL, Paris (FR)

(72) Inventors: Sébastien Thibaut, Puteaux (FR); Maria Dalko, Versailles (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/769,138

(22) PCT Filed: Oct. 20, 2016

(86) PCT No.: PCT/EP2016/075276
§ 371 (c)(1),
(2) Date: Apr. 18, 2018

(87) PCT Pub. No.: WO2017/068068
PCT Pub. Date: Apr. 27, 2017

(65) Prior Publication Data
US 2018/0303738 A1    Oct. 25, 2018

(30) Foreign Application Priority Data

Oct. 20, 2015    (FR) ..................................... 15 59999

(51) Int. Cl.
| | | |
|---|---|---|
| *A61K 8/60* | (2006.01) | |
| *A61Q 7/00* | (2006.01) | |
| *A61K 8/06* | (2006.01) | |
| *A61K 8/42* | (2006.01) | |
| *A61K 8/44* | (2006.01) | |
| *A61K 8/46* | (2006.01) | |

(52) U.S. Cl.
CPC ................ *A61K 8/602* (2013.01); *A61Q 7/00* (2013.01); *A61K 8/06* (2013.01); *A61K 8/42* (2013.01); *A61K 8/44* (2013.01); *A61K 8/46* (2013.01)

(58) Field of Classification Search
None
See application file for complete search history.

(56) References Cited

U.S. PATENT DOCUMENTS 7,049,300 B2 *    5/2006    Dalko .................... A61K 8/602
                                                             514/18.6

FOREIGN PATENT DOCUMENTS

| FR | 2 899 467 A1 | | 10/2007 |
|---|---|---|---|
| FR | 2 899 468 A1 | | 10/2007 |
| FR | 2 899 469 A1 | | 10/2007 |
| IN | 3923CHE2012 | * | 3/2014 |
| WO | WO2006090307 | * | 8/2006 |
| WO | WO-2013/184463 A1 | | 12/2013 |

* cited by examiner

*Primary Examiner* — Jennifer A Berrios
(74) *Attorney, Agent, or Firm* — Polsinelli PC

(57) ABSTRACT

This invention relates to the cosmetic use of at least one glycoside chosen from glycosides having the following general formula (I): Sacc-$(CH_2)_i$—X—R in order to increase the hair mass.

11 Claims, No Drawings

USE OF GLYCOSIDES TO INCREASE HAIR MASS

CROSS REFERENCE TO RELATED APPLICATIONS

This application is a National Phase filing under 35 U.S.C. § 371 of PCT/EP2016/075276 filed on Oct. 20, 2016; and this application claims priority to Application No. 15 59999 filed in France on Oct. 20, 2015 under 35 U.S.C. § 119. The entire contents of each application are hereby incorporated by reference.

This invention concerns a new cosmetic use of glycosides in the field of hair care. In particular, it concerns the cosmetic use of glycosides to thicken the hair.

Increasingly, in the field of hair care, users are looking for products that make it possible to increase the quality of the hair. In particular, there is an increasing need with regards to the sustainable thickening of fine hair, mainly in the zones where the population is aging, such as Europe, the United States and Japan.

Indeed, several studies show that after 40 years, the heterogeneity of the diameters of the hair present on the same scalp increases, especially in women, and that the average thickness tends to decrease.

It is known from document WO 2010/082001 that C-glycosides make it possible to increase hair growth (extending the length of hair).

Document FR 2 882 516 describes the use of C-glycosides to improve the resistance of hair (anti-breakage effect of C-glucosides on hair).

It is therefore necessary today to seek a technical solution that makes it possible to obtain compositions for the hair care field to improve the quality of the hair, and in particular by increasing the diameter of the hair, as such increasing the hair mass.

The present invention has for purpose to supply a cosmetic composition intended for the treatment of hair allowing the hair to be thickened.

As such, this invention relates to the cosmetic use of at least one glycoside chosen from glycosides having the following general formula (I):

$$\text{Sacc-(CH}_2\text{)}_i\text{—X—R} \quad \quad \text{(I)}$$

in which:

Sacc represents a monosaccharide or a polysaccharide comprising up to 20 sugar units, in the form of pyranose and/or furanose and L and/or D series, said mono- or poly-saccharide being possibly substituted by a necessarily free hydroxy group, and/or possibly one or several amine function(s) that are possibly protected;

i is 0 or 1;

X is a heteroatom, or is chosen from the group consisting of the —C($R_a$)=N—O—, —C(=O)—, —C(=S)—, —C(—$SR_a$) and —C($R_b$)($R_c$)— groups, $R_a$ representing H or a linear or branched ($C_1$-$C_6$)alkyl group, $R_b$ and $R_c$, are identical or different, representing H or a group chosen from the group consisting of hydroxy, alkoxy ($C_1$-$C_6$), alkoxy($C_1$-$C_6$)amino, alkoxy($C_1$-$C_6$)ammonium, alkoxy($C_1$-$C_6$)-diamino, amino, ($C_1$-$C_6$)alkylamino, di(($C_1$-$C_6$)alkyl)amino, hydroxy($C_1$-$C_6$)alkylamino, di(hydroxy ($C_1$-$C_6$)alkyl)amino, and (hetero)arylamino groups;

R represents a ($C_1$-$C_{10}$)alkyl, linear or branched group, said alkyl group being possibly substituted by at least one substituent chosen from the group consisting of $OR_a$, —C(O)OH and —C(O)OR''$_2$, R''$_2$ being a linear or branched ($C_1$-$C_4$)alkyl group; or R represents a ($C_1$-$C_4$)alkyl($C_6$-$C_{10}$)aryl group, said aryl group being possibly substituted by at least one substituent $OR_e$, $R_e$ representing H or a linear or branched ($C_1$-$C_6$)alkyl group;

the Sacc-(CH$_2$)$_i$—X bond representing a bond of a C-anomeric nature, which can be α or β, as well as the salts thereof, the solvates thereof such as hydrates and the optical and geometric isomers thereof, in order to increase the diameter of the fiber and as such increase the hair mass and/or the volume of hair.

According to an embodiment, this invention relates to the use of a glycoside having the aforementioned formula (I) to increase the diameter of hair fibers and as such increase the hair mass and/or the volume of hair.

In the formula (I) such as defined hereinabove, Sacc can represent a monosaccharide or a polysaccharide comprising up to 6 sugar units, in the form of pyranose and/or furanose and L and/or D series.

According to an embodiment, Sacc is a D series monosaccharide or polysaccharide.

According to an embodiment, Sacc represents a monosaccharide or a disaccharide, and preferentially Sacc is a monosaccharide.

According to an embodiment, Sacc is a D series monosaccharide or polysaccharide.

According to an embodiment, in the formula (I), Sacc is chosen from the group consisting of D-glucose, D-galactose, D-mannose, D-xylose, D-lyxose, L-fucose, L-arabinose, L-rhamnose, D-glucuronic acid, D-galacturoni acid, D-iduronic acid, N-acetyl-D-glucosamine, N-acetyl-D-galactosamine. Preferably, it is chosen from D-xylose, L-fucose, D-galactose and D-maltose.

Preferably, the glycoside used according to the invention is a compound having formula (I), wherein Sacc represents D-xylose.

A family of glycosides used according to the invention is comprised of modified xyloses, i.e. xyloses substituted by a —(CH$_2$)$_i$—X—R, i, X and R group being such as defined hereinabove.

These compounds have the following formula (II):

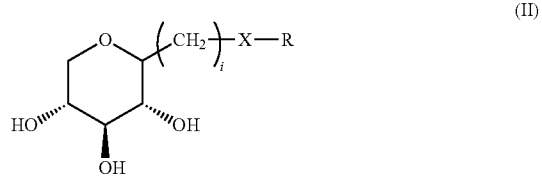

R, X and i being such as defined hereinabove.

Preferably, in the formula (II), i=1.

According to an embodiment, in the formula (I) or (II), X is a heteroatom chosen from O or S.

According to an embodiment, X represents a radical chosen from the —C(=O)—, —CH(OH)—, —CH(NH$_2$)—, —CH(NHCH$_2$CH$_2$CH$_2$OH)— groups, and in particular a —C(=O)—, —CH(OH)— or —CH(NH$_2$)— radical and more particularly a —CH(OH)— radical.

According to an embodiment, in the formula (I) or (II), X is —O—, —C(=O)—, —C(=S)—, —C(SR$_a$)—, —C(R$_a$)=N—O— or —C(R$_b$)(R$_c$)—, R$_a$, R$_b$ and R$_c$ such as defined hereinabove.

According to an embodiment, in the formula (I) or (II), X is —O—, —C(R$_a$)=N—O— or —C(R$_b$)(R$_c$)—, R$_a$, R$_b$ and R$_c$ being such as defined hereinabove.

According to an embodiment, $R_a$ represents H or a methyl group, preferably a methyl group.

According to an embodiment, $R_b$ and $R_c$, identical or different, represent H or a hydroxy group.

According to an embodiment, in the formula (I) or (II), X is —O—, —C(CH$_3$)=N—O— or —CH(OH)—.

A family of glycosides used according to the invention is comprised of xyloses substituted by a —X—R, X and R group being such as defined hereinabove. These compounds have the following formula (III):

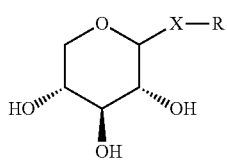
(III)

R and X being such as defined hereinabove.

According to an embodiment, in the formula (III), X is a heteroatom, and in particular —O—.

A family of glycosides used according to the invention is comprised of xyloses substituted by a —CH$_2$—X—R, X and R group being such as defined hereinabove. These compounds have the following formula (IV):

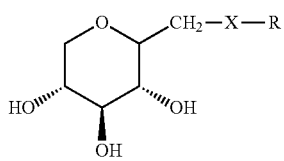
(IV)

R and X being such as defined hereinabove.

According to an embodiment, in the formula (IV), X is —C(R$_a$)=N—O— or —C(R$_b$)(R$_c$)—, R$_a$, R$_b$ and R$_c$ being such as defined hereinabove. Preferably, X is —CH(OH)— or —C(CH$_3$)=N—O—.

A family of glycosides used according to the invention is comprised of xyloses having the following formula (V):

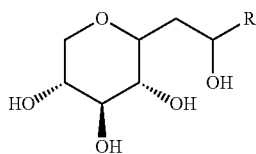
(V)

R being such as defined hereinabove.

These compounds correspond to compounds having formula (II) wherein i=1 and X is —CH(OH)—.

A family of glycosides used according to the invention is comprised of galactoses having the following formula (VI):

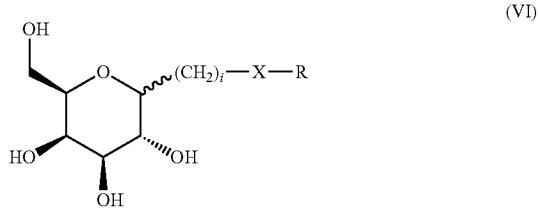
(VI)

i, X and R being such as defined hereinabove. According to an embodiment, X is —C=O in the formula (VI).

According to an embodiment, in the formulas (I), (II), (III), (IV), (V) and (VI) such as defined hereinabove, R represents a linear or branched (C$_1$-C$_{10}$)alkyl group, in particular C$_1$ to C$_4$, said alkyl group being possibly substituted by at least one substituent chosen from the group consisting of —OR$_a$, —C(O)OH and —C(O)OR"$_2$, R"$_2$ being a linear or branched (C$_1$-C$_4$)alkyl group and R$_a$ such as defined hereinabove. Preferably, R represents a linear or branched (C$_1$-C$_4$)alkyl group, not substituted.

According to an embodiment, in the formulas (I), (II), (III), (IV), (V) and (VI) such as defined hereinabove, R represents a (C$_1$-C$_4$)alkyl(C$_6$-C$_{10}$)aryl group, said aryl group able to be substituted by at least one substituent OR$_e$, R$_e$ representing H or a linear or branched (C$_1$-C$_6$)alkyl group.

The compounds having formula (I), (II), (III), (IV), (V) and (VI) can comprise one or several asymmetric carbon atoms. They can therefore exist in the form of enantiomers or diastereomers. The enantiomers, diastereomers, as well as mixtures thereof, including racemic mixtures, are part of the invention.

The compounds having formula (I), (II), (III), (IV), (V) and (VI) can exist in the form of bases or addition salts with acids. Such addition salts are part of the invention.

More particularly, this invention relates to the cosmetic use, in order to increase the diameter of hair fibers as well as the hair mass and/or volume of hair, of a glycoside having one of the following formulas:

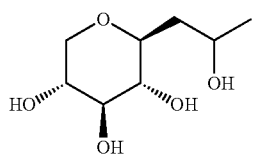

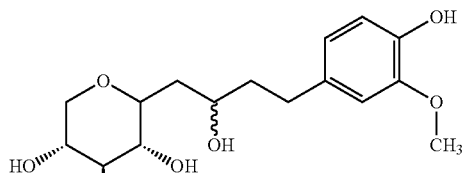

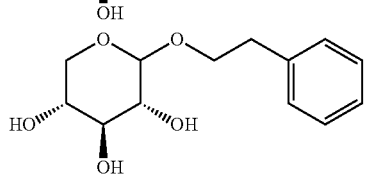

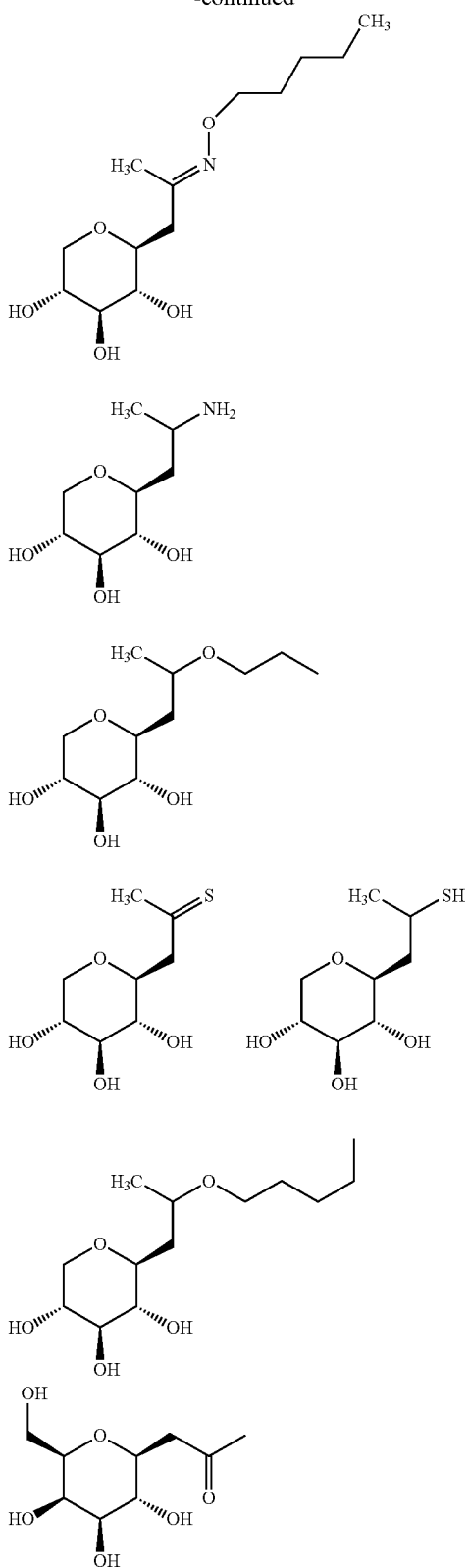

In particular, this invention relates to the cosmetic use of C-β-D-xylopyranoside-2-hydroxy-propane (or proxylane), in order to improve the quality of hair. Proxylane has the following formula:

According to an embodiment, the glycoside used according to the invention is present in a composition to be applied to the hair and/or the scalp. A composition useful to the invention comprises preferably a physiologically acceptable medium.

The term "physiologically acceptable medium" is intended to designate a medium compatible with the scalp and/or hair.

The physiologically acceptable medium is generally suitable for the nature of the support to which the composition should be applied, and also for the form in which the composition is to be packaged.

The cosmetically acceptable medium of the composition implemented is advantageously an aqueous medium. It can for example be constituted by water or by a mixture of water and of at least one cosmetically acceptable organic solvent. As an example of an organic solvent, mention can be made of ($C_2$-$C_4$) alcohols such as ethanol and isopropanol; polyols, in particular those having from 2 to 6 carbon atoms such as glycerin, propylene glycol, butylene glycol, pentylene glycol, hexylene glycol, dipropylene glycol, diethylene glycol; ethers of polyols such as 2-butoxyethanol, propylene glycol monomethyl ether, monoethylether and diethylene glycol monomethyl ether; and mixtures thereof.

The composition used according to the invention can further comprise one or several routine cosmetic additives, in particular chosen from non-ionic, anionic, cationic and amphoteric surfactants, vitamins and provitamins including pantenol, sunscreens, fillers, dyes, pearlescent agents, opacifiers, sequestering agents, polymers in particular film-forming, conditioning agents, plasticizers, thickeners, oils, antioxidants, anti-foaming agents, hydrating agents, emollients, penetration agents, perfumes and preservatives.

According to an embodiment of the invention, the glycoside is present in a cosmetic composition, at a rate of about 0.0001% to about 25% by weight with respect to the total weight of said composition, and in particular by about 0.001% to about 10%, preferably between 0.1% and 6% by weight of active material of glycoside with respect to the total weight of the composition.

The cosmetic compositions adapted to the implementation of the invention can be in the form of a suspension, gel, emulsion, shampoo, unrinsed lotion or foam.

The compositions can have all of the forms adapted for the care of the hair and/or the scalp, in particular in the form of a hair care lotion for example for daily or twice-weekly application, of a hair shampoo or conditioner, in particular for weekly or twice-weekly application, of a liquid or solid soap for cleansing the scalp for daily application, of a product for shaping hair (lacquer, styling gel), of a treating mask, of a cream or foaming gel for cleansing the hair.

A composition adapted to the implementation of the invention can have the form of an alcoholic or hydroalcoholic solution or aqueous suspension, or an oily suspension, an emulsion with a consistency that is more or less fluid and in particular liquid, semi-liquid or solid, obtained by dispersing a fatty phase in an aqueous phase (O/W) or conversely (W/O) or a multiple emulsion, an aqueous, hydro-alcoholic or oily gel, a loose or compact powder to be used as is or to be incorporated into a physiologically acceptable medium, microcapsules or microparticles, ionic or non-ionic dispersions.

Advantageously, the glycoside used according to the invention is applied in the form of a formulation that favors the penetration of the agent at the hair follicle. As an example, mention can be made of non-cyclic mono- and di-alcohols, ethyl acetate, butyl acetate, isopropyl myristate, fatty acids, phospholipids, terpenes, azone and derivatives, propylene glycol and glycol derivatives, cyclodextrins, octylsalicylate, cyclopentadecanolide, polysorbates, polyvinylpyrrolidone and derivatives, although this list not limiting.

According to an embodiment, the compositions contain a surfactant of the non-ionic, anionic, cationic or amphoteric type and among the latter, mention can be made of alkylsulfates, alkylbenzenesulfates, alkylethersulfates, alkylsulfonates, quaternary ammonium salts, alkylbetaines, oxyethylenated alkylphenols, fatty acid alkanolamides, oxyethylenated fatty acid esters as well as other non-ionic surfactants of the hydroxypropylether type.

When the compositions contains at least one surfactant, the latter is generally present at a maximum concentration of 30% by weight, and preferably, between 0.5% and 10% by weight with respect to the total weight of the composition.

With the purpose of improving the cosmetic properties of hair or to reduce or prevent the degradation thereof, the composition can also contain a treating agent of a cationic, anionic, non-ionic or amphoteric nature.

Among the treating agents mention can be made of linear or cyclival volatile or non-volatile silicones and mixtures thereof, polydimethylsiloxanes, quaternized polyorganosiloxanes such as those described in French patent application no. 2 535 730, polyorganosiloxanes with aminoalkyl groups modified by alcoxycarbonyalkyl groups such as those described in U.S. Pat. No. 4,749,732, polyorganosiloxanes such as the polydimethylsiloxane-polyoxyalkyl copolymer of the Dimethicone Copolyol type, a polydimethylsiloxane with stearoxy terminal groups (stearoxydimethicone), a polydimethylsiloxane-dialkylammonium acetate copolymer or a polydimethyl-siloxane polyalkylbetaine copolymer described in application GB 2 197 352, polysiloxanes organo-modified by mercapto or mercaptoalkyl groups such as those described in French patent no. 1 530 369 and in European patent application no. 0 295 780, as well as silanes such as stearoxytrimethylsilane.

The compositions according to the invention can also contain other ingredients such as cationic polymers, basic aminoacids (such as lysine, arginine) or acidic aminoacids (such as glutamic acid, aspartic acid), peptides and derivatives thereof, protein hydrolysates, waxes, as well as other compounds such as fatty alcohols, derivatives of lanolin, active ingredients such as panthothenic acid, agents against hair loss, anti-dandruff agents, thickeners, suspension agents, sequestering or complexing agents, opacifiers, sunscreens, antioxidants as well as perfumes and preservatives.

Throughout the application, the term "comprising a" or "including a" means "comprising at least one" or "including at least one", unless otherwise specified.

Throughout the above description, unless specified otherwise, the term "between x and y" refers to an inclusive range, i.e. the values x and y are included in the range.

EXAMPLES

Methodology

1. Origin of Hair Follicles

The hair follicles come from biopsies of human scalps, from cosmetic surgery operations conducted on white Caucasian women aged 45 to 75 years.

2. Dissection of Hair Follicles

The hair follicles are dissected according to the method described in patent application FR 2 736 721 and U.S. Pat. No. 5,712,169, and only the terminal anagen and pigmented hair follicles are studied.

3. Culturing Hair Follicles In Vitro

Freshly dissected hair follicles are introduced into multi-well plates containing 500 µL of William's medium, Invitrogen reference 22551022, enriched with insulin to 2 mM, 10 ng/mL of hydrocortisone, 10 µg/mL of L-Glutamine and 0.5% antibiotics (Gibco, reference 15240-096).

The C-glycosides are then incubated versus a vehicle alone (control condition), the hair follicles are placed in the incubator (37° C., 5% $CO_2$) and kept alive in these different conditions for 8 days. The culture mediums (of the treated and control conditions) are replaced every two days.

4. Treatments

Each glycoside is studied at 10 µM, (dilution of the solid compound in water), versus the vehicle alone (water) for the control condition.

Each condition is carried out on 12 different hair follicles, which makes it possible to overcome inter-follicle variabilities, and repeated over 3 different subjects (biopsies of scalp from 3 different volunteers) in order to evaluate the robustness of the results, and to overcome inter-donor variability.

The glycosides tested are as follows:

| NAME OF THE MOLECULE | STRUCTURE |
|---|---|
| 1 1,5-anhydro-6,8-dideoxy-L-gluco-octitol (Proxylane) | |
| 2 (3R,4S,5R)-2-[2-hydroxy-4-(4-hydroxy-3methhxyphenyl)butyl] tetrahydro-2Hpyran-3,4,5-triol | |

| NAME OF THE MOLECULE | STRUCTURE |
|---|---|
| 3 2-phenylethyl D-xylopyranoside | 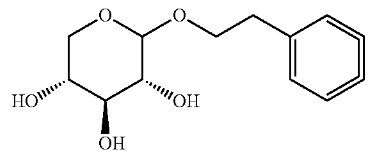 [SMILES: O[C@H]1[C@H](O)COC(OCCC2=CC=C=C=C2)[C@@H]1O] |
| 4 D-xylose | 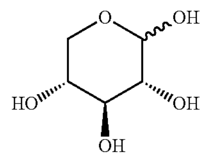 |

5. Evaluation of the Growth and of the Survival of the Hair Follicles

During the 8 days of treatment, all of the hair follicles are observed and photographed every two days in order to evaluate the maintaining of their survival. They are also measured using a binocular magnifier (Leica) provided with a micrometric eyepiece in order to ensure the proper growth thereof.

6. Measuring the Diameter of the Fiber

The diameter of the hair shaft is measured using photographs taken of all of the hair follicles at d0 and at d8. Using the Leica Application Suite software (Leica), the hair shaft is cropped, its surface is then calculated and its average diameter is determined. The increase in the diameter of the fiber generated in vitro is determined by: (average diameter at d8 Dd8−average diameter at d0 Dd0)*100/Dd0.

Results

The results hereinafter concern proxylane (PX) for 3 individuals.

| | average % of increase between D0 and D8 |
|---|---|
| Treatment - individual 1 | |
| Control | +9.7 |
| PX 1 mM | +17.5 |
| Treatment - individual 2 | |
| Control | +2.7 |
| PX 1 mM | +11.2 |
| Treatment - individual 3 | |
| Control | +4.3 |
| PX 1 mM | +14.5 |

| Treatment - individual 2 | average % of increase between D0 and D8 |
|---|---|
| Control | +2.7 |
| PX 1 mM | +11.2 |

| Treatment - individual 3 | average % of increase between D0 and D8 |
|---|---|
| Control | +4.3 |
| PX 1 mM | +14.5 |

For each subject, and increase in the thickness of the newly-formed hair shaft is observed in the presence of proxylane.

The same test as those described hereinabove were carried out for the aforementioned glycosides 2 to 4 and the values obtained are indicated hereinbelow:

| Glycoside | average % of increase of the diameter of the shafts |
|---|---|
| 2 | 12.7 |
| 3 | 16 |
| 4 | 11 |

It is therefore observed that these other glycosides also make it possible to significantly increase the thickness of the newly-formed hair shaft.

The invention claimed is:

1. A cosmetic method for increasing the diameter of hair fiber of an individual desiring such, which comprises applying to the scalp of said individual in order to increase the diameter of hair fiber at least one glycoside have the following formula (II):

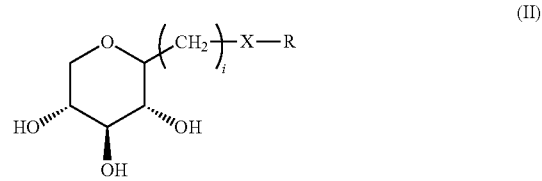

(II)

X being —O—, —C(Ra)=N—O— or —C(Rb)(Rc)-
i is 0 or 1;
$R_a$ representing H or a linear or branched $(C_1-C_6)$alkyl group,
$R_b$ and $R_c$, are identical or different, representing H or a group chosen from the group consisting of hydroxy, alkoxy ($C_1$-$C_6$), alkoxy($C_1$-$C_6$)amino, alkoxy($C_1$-$C_6$)ammonium, alkoxy($C_1$-$C_6$)-diamino, amino, ($C_1$-$C_6$)alkylamino, di(($C_1$-$C_6$)alkyl)amino, hydroxy($C_1$-$C_6$)alkylamino, di(hydroxy($C_1$-$C_6$)alkyl)amino, and (hetero)arylamino groups;

R represents a ($C_1$-$C_{10}$)alkyl, linear or branched, said alkyl group being possibly substituted by at least one substituent chosen from the group consisting of $OR_a$, —C(O)OH and —C(O)OR″$_2$, R″$_2$ being a linear or branched ($C_1$-$C_4$)alkyl group;

or R represents a ($C_1$-$C_4$)alkyl($C_6$-$C_{10}$)aryl group, said aryl group being optionally substituted by at least one substituent $OR_e$, $R_e$ representing H or a linear or branched ($C_1$-$C_6$)alkyl group;

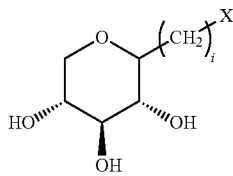

the bond representing a bond of a C-anomeric nature, which is α or β, as well as the salts thereof, the solvates thereof and the optical and geometric isomers thereof.

2. The cosmetic method according to claim 1, wherein X is —O—, —C(CH$_3$)=N—O— or —CH(OH)—.

3. The cosmetic method according to claim 1, wherein the glycoside is C-β-D-xylopyranoside-2-hydroxy-propane.

4. The cosmetic method according to claim 1, wherein the glycoside is present in a cosmetic composition, at a rate of about 0.0001% to about 25% by weight with respect to the total weight of said composition.

5. The cosmetic method according to claim 1, wherein the glycoside is implemented within a cosmetic composition adapted for topical administration.

6. The cosmetic method according to claim 5, wherein the composition is in the form of a suspension, gel, emulsion, shampoo, unrinsed lotion or foam.

7. The cosmetic method according to claim 1, for increasing the volume of the hair and/or hair mass.

8. The cosmetic method according to claim 2, wherein the glycoside is C-β-D-xylopyranoside-2-hydroxy-propane.

9. The cosmetic method according to claim 2, wherein the glycoside is present in a cosmetic composition, at a rate of about 0.0001% to about 25% by weight with respect to the total weight of said composition.

10. The cosmetic method according to claim 3, wherein the glycoside is present in a cosmetic composition, at a rate of about 0.0001% to about 25% by weight with respect to the total weight of said composition.

11. The cosmetic method according to claim 1, wherein the composition is applied to hair follicles of said individual.

* * * * *